(12) United States Patent
Fattom et al.

(10) Patent No.: US 7,449,189 B2
(45) Date of Patent: Nov. 11, 2008

(54) GLYCOCONJUGATE VACCINES FOR USE IN IMMUNE-COMPROMISED POPULATIONS

(75) Inventors: Ali I. Fattom, Rockville, MD (US); Robert B. Naso, Gaithersburg, MD (US)

(73) Assignee: NABI Biopharmaceuticals, Rockville, MD (US)

( * ) Notice: Subject to any disclaimer, the term of this patent is extended or adjusted under 35 U.S.C. 154(b) by 367 days.

(21) Appl. No.: 11/338,900

(22) Filed: Jan. 25, 2006

(65) Prior Publication Data

US 2006/0188518 A1    Aug. 24, 2006

Related U.S. Application Data

(63) Continuation of application No. 09/955,585, filed on Sep. 19, 2001, now abandoned.

(51) Int. Cl.
*A61K 39/385* (2006.01)
(52) U.S. Cl. .............................. 424/197.11; 424/243.1
(58) Field of Classification Search ............ 424/197.11, 424/243.1
See application file for complete search history.

(56) References Cited

U.S. PATENT DOCUMENTS 5,747,024 A * 5/1998 Grabstein et al. .......... 424/85.2

FOREIGN PATENT DOCUMENTS

WO    WO 98/10788    3/1998

OTHER PUBLICATIONS

Vaccine Weekly, Sep. 30, 1996, p. 10.*
Fattom et al (Vaccine, 13(14):1288-1293, 1995.*
Shinefield et al (New England Journal of Medicine 346(7):491-496, Feb. 14, 2002.*
Naso et al (Advances in Experimental Medicine and Biology, 397:133-140, 1996.*
A. Fattom et al.: 'Results from an efficacy study of Nabi® StaphVAX® (Staphylococcus aureus capsular polysaccharide (CP) conjugate vaccine) in hemodialysis patients', Abstracts of Papers American Chemical Society, 2001, vol. 221, No. 1-2, p. BIOT 45.
D. Gury and T. Mclain, Press Release, "*Nabi Reports Successful Reduction in S. Aureus Bacteremias at Interscience Conference on Antimicrobial Agents and Chemotherapy (ICACC)*," Sep. 19, 2000, Toronto, Canada.
Fattom et al., "Effect of Conjugation Methodology, Carrier Protein, and Adjuvants on the Immune Response to Staphylococcus Aureus Capsular Polysaccharides," Elsevier Science Ltd., Vaccine, vol. 13, No. 14, pp. 1288-1293, 1995.
Fattom et al., "Results From an Efficacy Study of Nabi® StaphVAX® (Staphylococcus Aureus Capsular Polysaccharide (CP) Conjugate Vaccine) in Hemodialysis Patients," Abstracts of Papers American Chemical Society, vol. 221, No. 1-2, p. 45, 2001.
Fattom et al., "Staphylococcal Vaccines: A Realistic Dream," Annals of Medicine, Finnish Medical Society, vol. 28, No. 1, pp. 43-46, 1996.
Fattom et al. "Staphylococcus Aureus Vaccination for Dialysis Patients—An Update," Advances in Renal Replacement Therapy, vol. 3, No. 4, 1996.
Naso et al., "Polysaccharide Conjugate Vaccines for the Prevention of Gram-Positive Bacterial Infections," Advances in Experimental Medicine and Biology, vol. 397, pp. 133-140, 1996.
Welch et al., "Safety and Immunogenicity of Staphylococcus Aureus Type 5 Capsular Polysaccharide-Pseudomonas Aeruginosa Recombinant Exoprotein A Conjugate Vaccine in Patients on Hemodialysis," Journal of the American Society of Nephrology, vol. 7, pp. 247-253, 1996.
Nabi Biopharmaceuticals Press Release, "Nabi Biopharmaceuticals Announces Results of StaphVAX® Confirmatory Phase III Clinical Trial," Nov. 1, 2005, 2 pages.
Search Report.
Shinefield, M.D., Henry et al., "Use of a *Staphylococcus aureus* Conjugate Vaccine in Patients Receiving Hemodialysis", *N. Engl. J. Med.*, vol. 346, No. 7, pp. 491-496, Feb. 14, 2002.
Ambrosino et al., "Response to *Haemophilus influenzae* Type B Conjugate Vaccine in Children Undergoing Splenectomy," Journal of Pediatric Surgery 27(8):1045-1048 (Aug. 1992).
Campbell et al., "Immunogenicity of a 24-Valent *Klebsiella* Capsular Polysaccharide Vaccine and an Eight-Valent *Pseudomonas* O-Polysaccharide Conjugate Vaccine Administered to Victims of Acute Trauma," Clinical Infectious Diseases, 23:179-181 (1996).
O'Brien et al., "Safety and Immunogenicity of Haptavalent Pneumococcal Vaccine Conjugated to $CRM_{197}$ Among Infacts With Sickle Cell Disease," Pediatrics 106(5):965-972 (Nov. 2000).
Robbins and Schneerson, "Polysaccharide-Protein Conjugates: A New Generation of Vaccines," The Journal of Infectious Diseases 161:821-832 (1990).
Shinefiled and Black, "Efficacy of pneumococcal conjugate vaccines in large scale field trials," Podiatr Infect Dis J. 19:394-397 (2000).
Sood et al., "Capsular polysaccharide-protein conjugate vaccines," Drug Discovery Today 1(9):381-387 (Sep. 1996).
The Dictionary of Immunology, Herbert et al. eds, Academic Press, 1995—Definition of Vaccine.

* cited by examiner

*Primary Examiner*—Patricia A Duffy
(74) *Attorney, Agent, or Firm*—Foley & Lardner LLP

(57) ABSTRACT

*Staphylococcal* and *Enterrococcal* glycoconjugate vaccines are disclosed for use in preventing or treating bacterial infection in an immune-compromised individual. Such vaccines contain an immunocarrier and a conjugate of a polysaccharide or glycopeptide surface antigen from a clinically-significant bacterial strain. The vaccines can be used for active protection in immune-compromised individuals who are to be subjected to conditions that place them at immediate risk of developing a bacterial infection, as would be case in the context of a catheterization or a surgical procedure.

18 Claims, No Drawings

GLYCOCONJUGATE VACCINES FOR USE IN IMMUNE-COMPROMISED POPULATIONS

BACKGROUND OF THE INVENTION

A. Field of the Invention

The invention relates generally to the use of staphylococcal and enterococcal glycoconjugate vaccines in preventing or treating bacterial infection in an immune-compromised individual.

B. Description of the Related Art

*Staphylococci* and *Enterococci* rarely cause systemic infections in otherwise healthy individuals, and therefore are considered opportunistic pathogens. Through various mechanisms, normal adult humans and animals with competent immune system attain an innate natural resistance to these bacterial infections. These include mucosal and epidermal barriers, in addition to possible immunological mechanisms. Interruption of these natural barriers as a result of injuries such as burns, traumas, or surgical procedures involving indwelling medical devices, increases the risk for staphylococcal and enterococcal infections. In addition, individuals with a compromised immune response such as cancer patients undergoing chemotherapy and radiation therapy, diabetes, AIDS, alcoholics, drug abuse patients, post organ transplantation patients and infants are at an increased risk for staphylococcal and enterococcal infections.

*Staphylococci* are commensal bacteria of the anterior nares, skin, and the gastrointestinal tract of humans. It is estimated that staphylococcal infections account for >50% of all hospital acquired infections. *S. aureus* alone is responsible for 15-25% of such infections and is surpassed only by *S. epidermidis* which accounts for 35% of these infections. Staphylococcal infections, especially those caused by *S. aureus* are associated with high morbidity and mortality.

*Staphylococcus* and *enterococcus* are a major cause of nosocomial and community-acquired infections, including bacteremia, metastatic abscesses, septic arthritis, endocarditis, osteomyelitis, and wound infections. For example, the bacteremia associated overall mortality for *S. aureus* is approximately 25 percent. A study of hospitalized patients in 1995 found that death rate, length of stay, and medical costs were twice as high for *S. aureus*-associated hospitalizations compared with other hospitalizations. *S. aureus* bacteremia is a prominent cause of morbidity and mortality in hemodialysis patients with an annual incidence of three to four percent. Contributing to the seriousness of *S. aureus* infections is the increasing percentage of isolates resistant to methicillin, and early reports of resistance to vancomycin. Hence, immunoprophylaxis against *S. aureus* is highly desired.

The capsular polysaccharides (CPS) of *S. aureus* are virulence factors in systemic infections caused by this opportunistic pathogen. *S. aureus* CPS confer invasiveness by inhibiting opsonphagocytic killing by polymorphonuclear neutrophils (PMN), similar to other encapsulated bacteria, such as *Streptococcus pneumoniae*. This enables the bacteria to persist in the blood, where they elaborate several different virulence factors, including toxins and extracellular enzymes. Of the 11 known types of *S. aureus*, Types 5 and 8 account for approximately 85 percent of all clinical isolates. Most of the remaining isolates carry a more-recently identified antigen known as Type 336. Antibodies to Types 5, 8 and 336 CPS induce type-specific opsonophagocytic killing by human PMNs in vitro, and confer protection in animal infection models.

*Staphylococci* have developed very sophisticated mechanisms for inducing diseases in humans, including both intracellular and extracellular factors. For instance, *S. aureus* possesses other surface antigens that facilitate its survival in the blood stream by helping the bacteria to evade phagocytic killing by the host leukocytes. These surface antigens include cell wall components such as teichoic acid, protein A, and capsular polysaccharides (CPS). Due in part to the versatility of these bacteria and their ability to produce extracellular products that enhance infectivity and pathogenesis, staphylococcal bacteremia and its complications such as endocarditis, septic arthritis, and osteomyelitis continue to be serious and frequently observed nosocomial infections.

Antibiotics such as penicillin have been used successfully against both staphylococcal and enterococcal infections in humans, but more recently the effectiveness of such antibiotics has been thwarted by the ability of bacteria to develop resistance. For example, shortly after the introduction of methicillin, a newer synthetic antibiotic, strains of methicillin-resistant *S. aureus* were isolated. Antibiotic resistance among staphylococcal isolates from nosocomial infections continues to increase in frequency, and resistant *S. aureus* strains continue to cause epidemics in hospitals in spite of developed preventive procedures and extensive research into bacterial epidemiology and antibiotic development. *Enterococci* resistant to vancomycin are now emerging, and methicillin-resistant *S. aureus* organisms with intermediate resistance to vancomycin have been identified in some centers. Cross transfer of resistance will eventually lead to the widespread development of organisms that are more difficult to eradicate.

The initial efficacy of antibiotics in treating and curing *Staphylococcal* infections drew attention away from immunological approaches for dealing with these infections. Although multiple antibiotic-resistant strains of *S. aureus* have emerged, other strategies such as vaccines have not been developed. In addition, passive immunization has been tested for use in immune-compromised individuals, such as neonates, who are at increased risk for contracting these bacterial infections. The data failed to support a solid conclusion in recommending the use of passive immunization in this population. Baker et al., *New Engl. J. Med.* 35:213-219 (1992); Fanaroff et al., *New Engl. J. Med.* 330:1107-1113 (1994). The use of active vaccination as an effective technique for protection of immune-compromised populations has not been realized as yet with any of the licensed vaccines. Vaccines that are immunogenic in healthy vaccinees are often found to be less or nonimmunogenic in immunocompromised patients, and thus to provide an insufficient level of protection. For example, the immune response of hemodialysis patients to hepatitis B vaccine was shown to be reduced to 50-80% of that seen in healthy vaccinees. Similarly, the immune response of elderly patients to this vaccine was reduced to 46%. Pirofski and Casadevall, *Clin. Microbiol. Rev.* 11:1-26 (1998).

Bacterial capsular polysaccharides are generally poor immunogens. Their immunogenicity in humans is known to be related to their molecular size and the age of the vaccinee. Infants below the age of two years, the elderly, and other immune-compromised patients are typically poor responders to CPS vaccines. While polysaccharide vaccines have been developed for some primary bacterial pathogens that induce acute diseases in normal individuals, namely, *Streptococcus pneumoniae, Neisseria meningitidis* and *Hemophilus influenzae*, none have been described specifically for treatment of opportunistic bacteria. Furthermore, when these vaccines were tested in immune-compromised individuals, a rapid decline in the immune response was observed, resulting in a lack of effective protection. In the case of *S. pneumoniae*, the vaccine tested included multiple strains, and worked in immunocompetent adults but not in immune-compromised individuals with poor immune response such as the elderly and AIDS patients. In the case of a *S. aureus* Type 5 conjugate vaccine, hemodialysis patients elicited lower maximal level amounts of antibodies compared to those elicited in healthy vaccinees, 180 ug/mil and 318 ug/ml, respectively. Moreover, a decline in antibody level occurred much more rapidly in dialysis patients than antibody levels in healthy vaccinees. After 6 months, antibody level in dialysis patients declined 39%, versus a 14% decline in healthy subjects. Welch et. al., *J. Am. Soc. Neph.* 7:247-253 (1996).

Live vaccines generally are more immunogenic, but present a concern when vaccinating immune-compromised patients. Although the viral and bacterial strains used in such vaccines are attenuated, some of the strains can revert back and cause disease. Immunization with a bacterial component vaccine especially is preferred for immune-compromised patients, such as chemotherapy patients, hemodialysis patients, infants, shock trauma patients, surgical patients, and others with reduced resistance or partially compromised immune systems.

Polysaccharide antigens normally generate a T-cell independent immune response and they induce humoral antibodies with no boost of the immune response observed upon reinjection. To generate a complete immune response, conjugation of polysaccharide to protein carriers can alter bacterial CPS antigens to make them T-cell dependent immunogens, thus increasing their immunogenicity and potentiating their use in infants and immune-compromised patients.

Immune-compromised individuals often are at high risk for bacterial infections, for example, from procedures such as catheterization. Given their poor immune response, exposure to an infectious strain of bacteria is likely to lead to a high level of infection. The fact that many bacterial strains have developed resistance to many or all current antibiotics increases the likelihood of a negative outcome when an immune-compromised individual does develop a bacterial infection. Therefore, it would be highly desirable to vaccinate immune-compromised against common clinically-significant bacterial strains. However, bacterial antigens such as the staphylococcal and enterococcal polysaccharide antigens are known to be poor immunogens. Their immunogenicity can be enhanced by conjugation to carrier proteins, but none of the currently available conjugate vaccines have ever been shown to be effective in immune-compromised patients, and it is widely accepted that these vaccines would be unable to produce an effective immune response in an immune-compromised population.

SUMMARY OF THE INVENTION

The present inventors have found that conjugates of certain staphylococcal and enterrococcal polysaccharide and glycopeptide bacterial surface antigens, denoted herein as "glycoconjugates," are effective in protecting against bacterial infection in immune-compromised individuals. For example, bivalent vaccines containing *S. aureus* Types 5 or 8 CPS bound to recombinant exoprotein A (rEPA), a nontoxic variant of *Pseudomonas aeruginosa* exotoxin A expressed in *Escherichia coli*, were immunogenic and well-tolerated in healthy adults and in patients with end-stage renal disease (ESRD), and, more importantly, were able to prevent bacteremia in ESRD hemodialysis patients. This was entirely unexpected in light of conventional theory to the effect that immune-compromised individuals cannot be expected to mount an effective immune response against poorly immunogenic antigens such as polysaccharide antigens, which are known for their generally low immunogenicity.

Immunologically, ESRD patients on hemodialysis are the patients with the most severe conditions among at-risk adult populations. They are mostly elderly, many are diabetic (~50%), and they routinely suffer from uremia. Uremia and hyperglycemia have a major debilitating impact on host defense mechanisms, especially opsonophagocytosis. These conditions cause major impairment of immune function via impaired complement or phagocyte functionality. ESRD patients typically have depressed neutrophil function and impaired phagocytosis, leukopenia secondary to complement activation, reduced natural killer cell activity, decreased T and B lymphocyte function, and decreased T lymphocyte response to standard antigens. The ability of vaccines according to the invention to protect such a highly immune-compromised target population could not have been predicted.

The present invention comprehends the protecting of an immune-compromised human from at least one of *Staphylococcal* and *Enterococcal* bacterial infection. The vaccine comprises a glyconjugate of a polysaccharide or glycopeptide bacterial surface antigen and an immunocarrier. The inventive approach entails administering the vaccine to immune-compromised individuals in a dose that produces a serotype-specific antibody level in the immune-compromised individual that is comparable to that achievable in normal healthy subjects in response to the vaccine. The vaccine comprises:

(a) glycoconjugates of both Type 5 and Type 8 polysaccharide antigens of *S. aureus*, (b) a glycoconjugate of a negatively-charged *Staphylococcal* polysaccharide antigen that comprises β-linked hexosamine as a major carbohydrate component and contains no O-acetyl groups, (c) a glycoconjugate of *Staphylococcal* glycopeptide antigen that comprises amino acids and a N-acetylated hexosamine in an α configuration, that contains no O-acetyl groups, and that contains no hexose, (d) a glycoconjugate of an acidic *Staphylococcal* polysaccharide antigen that is obtained from an isolate of *S. epidermidis* that agglutinates antisera to ATCC 55254, (e) a glycoconjugate of an *E. faecalis* antigen that comprises 2-acetamido-2-deoxy-glucose and rhamnose in a 1:2 molar ratio, (f) a glycoconjugate of an *E. faecalis* antigen that comprises a trisaccharide repeat which comprises a 6-deoxy sugar, (g) a glycoconjugate of an *E. faecium* antigen that comprises 2-acetamido-2-deoxy-galactose and galactose in a 2:1 molar ratio, (h) a glycoconjugate of an *E. faecium* antigen that reacts with antibodies to ATCC 202016, or (i) a glyconcojugate of an *E. faecium* antigen that reacts with antibodies to ATCC 202017.

The vaccine produces in immune-compromised individuals a level of serotype-specific antibody to the antigens contained in the vaccines that is the same, within the limits of expected experimental variation, to the level that is achieved in normal healthy subjects when they are immunized with a vaccine that contains glyconjugates.

DETAILED DESCRIPTION OF SPECIFIC EMBODIMENTS

It has been discovered that immune-compromised individuals can be protected effectively against bacterial infection by administering a vaccine that contains, with an immunocarrier, a conjugate of a polysaccharide or glycopeptide surface antigen from a clinically-significant staphylococcal or enterococcal bacterial strain. In the present context, a "clinically-significant" bacterial strain is one that is pathogenic in humans. The vaccine can be used for active protection in immune-compromised individuals that are about to be subjected to conditions which place them at immediate risk of developing a bacterial infection. These conditions would include, for example, catheterization or a surgical procedure. Notably, the present inventors found that immune-compromised individuals mounted an effective immune response when vaccinated with a vaccine according to the present invention.

Immune-compromised individuals may suffer a deficiency with respect to either or both of the cellular and the humoral arm of the immune system. Both of these arms combat infectious diseases. Bacterial infections, in particular, are cleared mainly by two mechanisms: bactericidal activity, which requires both antibodies and complement, and opsonophagocytosis, which requires phagocytes in addition to complement and antibodies. Each of the steps in these processes may suffer from a defect that will impact to a different extent the functionality of the whole process, any such defect results in a host that is "immune-compromised."

ESRD patients provide an excellent model for predicting the ability of a vaccine to protect an immune-compromised, because so many aspects of the immune response are compromised in such patients. For example, many of these patients have diabetes, or hyperglycemia, which interferes with complement fixation. The inability to fix complement limits the usefulness of antibodies in these patients. Moreover, phagocytes may, as a result of diabetes, have weakened chemotactic movement which, in turn, may result in their inability to reach the location of an infection. Hemodialysis patients also suffer from uremia which impacts the functionality of granulocytes and complement fixation, resulting in inefficient opsonophagocytosis. Diabetes and uremia also impact the functionality of B cells that results in lower than optimal immune response to vaccination.

In the present context, a polysaccharide or glycopeptide surface antigen is one that contains a major proportion of carbohydrate residues. Antigens that comprise only carbohydrate residues are referred to as polysaccharide antigens. Some bacterial surface antigens additionally contain a smaller proportion of amino acid residues, typically less than 40% by weight of the antigen, in which case they are referred to as glycopeptide antigens. Bacterial surface antigens according to the present invention may be capsular polysaccharides, or they may comprise teichoic acid.

A variety of staphylococcal and enterococcal bacterial surface antigens have been identified as suitable for preparation of a conjugate vaccine according to the present invention. In particular, these include polysaccharide and glycopeptide antigens found on various strains of *S. aureus, S. epidermidis, S. haemolyticus* or *S. hominis, E. faecium* and *E. faecalis*.

Antigens for the preparation of a conjugate vaccines according to the present invention include the Type 5 and Type 8 antigens of *S. aureus*. Surveys have shown that approximately 85-90% of isolates are capsular polysaccharide Type 5 or Type 8. Normal individuals vaccinated with a vaccine containing Type 5 and Type 8 capsular polysaccharide antigens are protected from infection by 85-90% of *S. aureus* strains. The structures of Types 5 and 8 polysaccharide antigens have been elucidated by Moreau et al., *Carbohydr. Res.* 201:285 (1990); and Fournier et al., *Infect. Imm.* 45:87 (1984). Both have FucNAcp in their repeat unit as well as ManNAcA which can be used to introduce a sulfhydryl group. The structures are as follows:

Type 5:

->4)-β-D-ManNAcAp(1-->4)-α-L-FucNAcp(1-->3)-β-D-FucNAcp(1-3)Oac

Type 8:

->3)-β-D-ManNAcAp(1-->3)-α-L-FucNAcp(1-->3)-β-D-FucNAcp(1-4) Oac

A preferred vaccine according to the present invention includes conjugates of both the Type 5 and Type 8 antigens. It is particularly surprising that this bivalent vaccine provides an excellent level of protection in immune-compromised individuals. Welch et al (1996), supra, discloses that a monovalent Type 5 vaccine produces a very limited immune response in ESRD patients. The protection achieved with a bivalent Type 5/Type 8 *S. aureus* vaccine according to the present invention could not have been forseen based on the poor result reported in Welch et al., particularly when coupled with a teaching in the art that the addition of a second component antigen to a vaccine actually decreases the efficacy of each component individually. Fattom et al. 17:126-133 (1999).

Another *Staphylococcus* antigen that can be used in the preparation of conjugates according to the invention is described in U.S. Pat. No. 5,770,208 and No. 6,194,161. This negatively-charged antigen comprises β-linked hexosamine as a major carbohydrate component, and contains no O-acetyl groups detectable by nuclear magnetic resonance spectroscopy. The antigen specifically binds with antibodies to *S. aureus* Type 336 deposited under ATCC 55804. *S. aureus* strains that carry this antigen account for nearly all of the clinically significant strains of *S. aureus* that are not Type 5 or Type 8 strains. Thus, it is particularly advantageous to use this antigen in combination with *S. aureus* Type 5 polysaccharide antigen and *S. aureus* Type 8 polysaccharide antigens to provide nearly 100% coverage of *S. aureus* infection.

There are also many clinically significant strains of *S. epidermidis*. In order to protect against or treat infection by these strains, a conjugate vaccine prepared with a so-called Type 1 antigen as disclosed in U.S. Pat. Nos. 5,961,975 and 5,866,140 is preferred. This antigen is an acidic polysaccharide antigen that is obtained by a process that comprises growing cells of an isolate of *S. epidermidis* that agglutinates antisera to ATCC 55254 (a Type I isolate); extracting polysaccharide antigen from the cells to produce a crude extract of polysaccharide antigen; purifying this crude extract to produce purified antigen that contains less than 1% protein; loading the purified antigen on a separatory column and eluting it with a NaCl gradient; and identifying fractions containing the polysaccharide antigen using antibodies specific to a Type I isolate.

Yet another *Staphylococcus* antigen for the preparation of conjugate vaccines according to the present invention is described in WO 00/56357. This antigen comprises amino acids and a N-acetylated hexosamine in an α configuration, contains no O-acetyl groups detectable by nuclear magnetic resonance spectroscopy, and contains no hexose. It specifically binds with antibodies to a *Staphylococcus* strain deposited under ATCC 202176. Amino acid analysis of the antigen shows the presence of serine, alanine, aspartic acid/asparagine, valine, and threonine in molar ratios of approximately 39:25:16:10:7. Amino acids constitute about 32% by weight of the antigen molecule.

In addition to conjugate vaccines with these *Staphylococcus* antigens, conjugate vaccines with *Enterococcus* antigens as described in WO 99/18996 are preferred according to the invention. This application discloses five different antigens, two of which are isolated from *E. faecalis* strains and three of which are isolated from *E. faecium* strains. Representatives of each of the two *E. faecalis* and three *E. faecium* strains have been deposited under the Budapest Treaty with the American Type Culture Collection, and have been given Accession Nos. 202013 (*E. faecalis* EFS1), 202014 (*E. faecalis* EFS2), 202015 (*E. faecium* EFM3), 202016 (*E. faecium* EFM4), and 202017 (*E. faecium* EFM5), respectively. Antigen for use in the present invention can be isolated from the deposited strains, or the deposited strains can be used to identify other strains which express antigen according to the invention, from which antigen may be extracted and purified. One of the *E. faecalis* antigens, EFS 1, comprises 2-acetamido-2-deoxy-glucose, rhamnose, glucose and 2-acetamido-2-deoxy-galactose in an approximate calculated molar ratio of 1:2:2:2, another *E. faecalis* antigen, EFS2, comprises a trisaccharide repeat which comprises a 6-deoxy sugar, and an *E. faecium* antigen, EFM3, comprises 2-acetamido-2-deoxy-galactose and galactose.

Each of the foregoing antigens can be obtained in recoverable amount, from certain *Staphylococcus* and *Enterococcus* isolates cultured pursuant to the protocols described in the cited documents, in substantially pure form. In particular, the purified antigens contain less than 1% nucleic acids. A "recoverable" amount in this regard means that the isolated amount of the antigen is detectable by a methodology less sensitive than radiolabeling, such as immunoassay, and can be subjected to further manipulations involving transfer of the antigen per se into solution.

For use as a vaccine in an immune-compromised populations according to the present invention, an antigen is conjugated to an immunocarrier. An immunocarrier is a substance, usually a polypeptide or protein, which improves the interaction between T and B cells for the induction of an immune response against the antigen and thus enhances immunogenicity both for active immunization and for preparing high-titered antisera in volunteers for use in subsequent passive immunization. Suitable immunocarriers according to the present invention include tetanus toxoid and diphtheria toxoid and recombinantly produced, genetically detoxified variants thereof, *Staphylococcal* exotoxin or toxoid, *Pseudomonas aeruginosa* Exotoxin A or its derivatives, including particularly recombinantly-produced non-toxic mutant strains of *Pseudomonas aeruginosa* Exotoxin A, as described, for example, in Fattom et al., *Inf. and Imm.* 61: 1023-1032 (1993), as well as other proteins commonly used as immunocarriers.

In order to conjugate the antigen to a carrier protein, the antigen is first derivatized. Various methods can be used to derivatize antigen and covalently link it to an immunocarrier. Activated carboxylate groups of the antigen can be derivatized with ADH, cystamine or PDPH, and then the antigen can be coupled to a carrier protein either by a carbodiimide-mediated reaction of the partially-amidated antigen to a carboxylate group on the carrier protein or by disulfide interchange of thiolated antigen with an SPDP-derivatized carrier protein.

Hydroxyl groups on the antigen can be activated using cyanogen bromide or 1-cyano-4-dimethylamino-pyridinium tetrafluoroborate, and then the antigen can be derivatized with the six carbon bifunctional spacer adipic acid dihydrazide (ADH), according to techniques known in the art, according to the method of Kohn et al. *FEBS Lett.* 154: 209:210 (1993). This material then is linked to diphtheria toxoid (Dtd), recombinant exoprotein A from *Pseudomonas aeruginosa* (rEPA), tetanus toxoid (TTd) or another suitable carrier protein by 1-ethyl-3-(3-dimethylaminopropyl) carbodiimide (EDAC). The resulting conjugates can be separated from unreacted antigen by size exclusion chromatography. Regardless of the method used to conjugate the antigen to the carrier protein, covalent linking of the antigen to the carrier protein significantly enhances the immunogenicity of the antigen, and results in increased levels of antibodies to the antigen after both the first and second boost in mice.

The antigen-immunocarrier conjugate according to the present invention is the active ingredient in a composition, further comprising a pharmaceutically acceptable carrier for the active ingredient, and is used as a vaccine to induce a cellular immune response and/or production in vivo of antibodies which combat bacterial infections in immune-compromised populations, particularly *Staphylococcus* and/or *Enterococcus* infections. In this regard, a pharmaceutically acceptable carrier is a material that can be used as a vehicle for administering a medicament because the material is inert or otherwise medically acceptable, as well as compatible with the active agent, in the context of vaccine administration. In addition to a suitable excipient, a pharmaceutically acceptable carrier can contain conventional vaccine additives like diluents, adjuvants and other immunostimulants, antioxidants, preservatives and solubilizing agents.

The vaccine according to the invention can be administered with or without an adjuvant. If an adjuvant is used, it is selected so as to avoid adjuvant-induced toxicity. A vaccine according the invention additionally may comprise a β-glucan or granulocyte colony stimulating factor, in particular, a β-glucan as described in U.S. application Ser. No. 09/395,360, filed Sep. 14, 1999.

Preferably, a composition of the antigen/immunocarrier conjugate according to the present invention "consists essentially of" the conjugate. In this context, the phrase "consists essentially of" means that the composition does not contain any material that interferes with elicitation of an immune response to the antigen (and to other antigens, if present) when the composition is administered to a subject as a vaccine.

There are a large number of immune-compromised populations which benefit from the administration of vaccines according to the present invention. These include end stage renal disease (ESRD) patients; cancer patients on immunosuppressive therapy, AIDS patients, diabetic patients, the elderly in extended care facilities, patients with autoimmune disease on immunosuppressive therapy, transplant patients, and burn patients. The immune system is composed of two arms, the cellular and the humoral arm. Both of these arms combat infectious diseases. Bacterial infections in particular are cleared mainly by two mechanisms. Bactericidal activity which includes antibodies and complement, and opsnophagocytosis which in addition to complement and antibodies, phagocytes are essential. Each of these steps in these processes may suffer from a defect that will impact to a different extent the functionality of the whole process. Any such defect make the host an immunocompromised person. Examples for such unfunctional or compromised mechanisms can occur as a result of diabetes. Diabetes or hyperglycemia interferes with the complement fixation. So even if a person have enough antibodies, the inability to fix complement render these antibodies of limited use. Moreover, phagocytes may, as a result of diabetes, have weakened chemotactic movement which, in turn, may result in their inability to reach the location of an infection. Hemodialysis patients suffer from uremia which impacts the functionality of granulocytes and complement fixation, resulting in inefficient opsonophagocytosis. Moreover, diabetes and uremia impact the functionality of B cells that results in lower than optimal immune response to vaccination.

The present invention is further described by reference to the following, illustrative examples.

EXAMPLE 1

Dosing Studies of *S. aureus* Type 5/Type 8 Polysaccharide Vaccine in Patients with ESRD Twenty adult male end stage renal disease (ESRD) patients being maintained on either chronic ambulatory peritoneal dialysis or hemodialysis each patient received a single intramuscular injection of vaccine formulated to contain a target dose of 25 μg each of Type 5 and Type 8 *S. aureus* CPS formulated as a recombinant *Pseudomonas* exoprotein (rEPA) protein conjugate. This 25 μg dose is the same as that used in healthy subjects. A second 0.5 mL dose of bivalent vaccine was given six (6) weeks after the first dose because of the anticipated weaker immune response in this chronically-ill population. Five (5) additional healthy adult males received an equivalent volume of saline placebo. Anti-type 5 and 8 CPS IgG levels were assessed before injection and at 2 and 6 weeks post-injection.

As shown in Table 1, a substantial immune response was seen in the ESRD patients, even though it was less in ESRD patients than in normal healthy subjects. The second dose administered at six (6) weeks had virtually no impact on antibody levels specific for either serotype.

TABLE 1

Immunogenicity of *S. aureus* T5/T8 CPS Vaccine at a Nominal Dose of 25 μg of Each CPS in Adult Males with ESRD

| | N | Day 0 | Week 6 | Week 12 | % resp. at week 6, 12 | Day 0 | Week 6 | Week 12 | % resp. at week 6, 12 |
|---|---|---|---|---|---|---|---|---|---|
| | | Geo. mean Type 5-specific IgG, μg/mL | | | | Geo. Mean Type 8-specific IgG, μg/mL | | | |
| Vaccine group | 15 | 5.4 | 61.9 | 52.6 | 80, 80 | 10.4 | 30.8 | 31.0 | 47, 40 |
| Placebo group | 5 | 6.0 | 5.4 | 5.9 | 0, 0 | 18.6 | 17.2 | 18.1 | 0, 0 |

A dosing study in ESRD patients on hemodialysis next was undertaken based on the results of Table 1. A formulation containing 75 μg of Type 5 CPS and 55 μg of Type 8 CPS (each conjugated to an equal weight of rEPA) in a volume of 1.0 mL was used. Thirty-three adult ESRD patients, including both sexes and maintained on hemodialysis, were immunized with single IM doses of *S. aureus* Type 5/Type 8 CPS Conjugate Vaccine/IA. An initial group of 16 subjects received a 1.0 mL dose (75 μg of Type 5 and 55 μg of Type 8). After this group was observed for safety for one week, an additional 17 subjects received a 1.5 mL dose (118 μg of Type 5 and 83 μg of Type 8). Both doses were well-tolerated. Serotype-specific IgG levels were monitored 2 and 6 weeks and 3, 6, 9, and 12 months post-injection.

In comparison with Table 1, both dosing levels gave improved peak serotype-specific antibody levels at six weeks post-injection and, importantly, recruited a markedly larger fraction of anti-type 8 responders (Table 2). Serotype-specific antibody to both CPS types approached levels achievable in normal healthy subjects in recipients of the 1.5 mL dose, and remained a geometric mean of 6.03-fold (for Type 8) to 10.28-fold (for Type 5) elevation over baseline values at one year ($p<0.0001$ for both serotypes.)

TABLE 2

Immunogenicity of *S. aureus* T5/T8 CPS Vaccine at Increased Doses in Adults with ESRD Maintained on Hemodialysis

| Dose (μg Type 5/ μg Type 8) | N | Geo. mean Type 5-specific IgG (μg/mL) | | % Type 5 resp. | Geo. mean Type 8-specific IgG (μg/mL) | | % Type 8 resp. |
|---|---|---|---|---|---|---|---|
| | | Day 0 | Week 6 | | Day 0 | Week 6 | |
| 25/25 | 15 | 5.6 | 61.9 | 80.0 | 10.2 | 30.8 | 47.0 |
| 75/55 | 16 | 4.0 | 81.8 | 75.0 | 3.3 | 50.1 | 75.0 |
| 118/83 | 17 | 3.8 | 176.4 | 88.2 | 6.1 | 142.9 | 88.2 |

EXAMPLE 2

Protection of Patients with ESRD with *S. aureus* Type 5/Type 8 Polysaccharide Vaccine Subjects were recruited at 73 hemodialysis centers in California. Inclusion criteria were: age 18 years or older, ESRD on hemodialysis using a native vessel fistula or a synthetic/heterologous graft access for at least 8 weeks prior to enrollment, Karnofsky score of at least 50 at entry, and expected to complete the required follow-up visits. Exclusion criteria were: symptoms or signs consistent with an infection within the 2 weeks prior to vaccination, history of HIV infection, hypersensitivity or previous anaphylaxis caused by polysaccharide or polysaccharide-conjugate vaccines, drug abuse in the past year, use of immunosuppressive or immunomodulatory drugs, and malignancy or treatment for malignancy within 6 months prior to vaccination.

Eligible subjects were assigned randomly to receive a single injection of vaccine or placebo. Randomization was stratified by (1) vascular access (native-vessel fistula or synthetic/heterologous graft) and (2) presence or absence of persistent *S. aureus* nasal carriage.

The vaccine (StaphVAX®, supplied by Nabi, Rockville, Md.) was composed of *S. aureus* Type 5 and Type 8 CPS (100 μg/type/mL) conjugated to an equal weight of recombinant *Pseudomonas aeruginosa* non-toxic exotoxin A (rEPA), in 0.01 percent polysorbate 80 and sodium phosphate-buffered saline, pH 7.4. This dose was selected on the basis of studies in patients with ESRD (Nabi, unpublished data). Vaccine and placebo (sodium phosphate-buffered saline) were supplied as 1 mL of clear liquid in identical vials, each bearing a unique code.

In two screening visits approximately 1 week apart, subjects were evaluated for eligibility, and the anterior nares cultured for *S. aureus*. Carriage was defined by two positive cultures. The vaccine or placebo was administered by intramuscular injection into the deltoid or the anterior thigh.

Subjects were evaluated 30 minutes after the injection and instructed to record local (redness, swelling, aching, burning, tenderness, heat) and systemic (fever, general discomfort, muscle ache, headache, nausea, vomiting) reactions each day for 1 week. One week after injection, subjects returned to the dialysis center and vaccine reactions were recorded. Subjects were evaluated for adverse events up to 6 weeks after the injection. Deaths and all bacteremias were recorded until the study ended or the subject withdrew. The primary outcome measure was a subject's first occurrence of *S. aureus* bacteremia. Blood cultures were obtained before beginning antibiotic therapy.

Sera were obtained prior to and 6, 26, 54, and 67 weeks after vaccination. Antibodies to the *S. aureus* Type 5 and Type 8 CPS were measured by ELISA, as described in Fattom et al., *Infect Immun* 1990; 58:67-74 and Fattom et al., *Infect Immun* 1993;61:1023-32. A vaccine response was defined as a concentration of antibody of at least 25 µg/mL and at least twofold greater than the prevaccination level.

Surveys in the US and Europe suggested an incidence rate of 0.03-0.04 *S. aureus* bacteremias per hemodialysis patient-year. See, for example, Kessler et al., *Nephron* 1992;64:95-100; Quarles et al., *Am J Kidney Dis* 1985;6:412-9; Roubicek et al., *Nephrologie* 1995; 16:229-32; and Bloembergen and Port, *Adv Ren Replace Ther* 1996;3:201-7. With an adjusted type I error of 0.042 (Fleming-O'Brien method, *Biometrics* 1979;35:549-56.), a sample size of 900 subjects per group was determined to be sufficient to detect, with 80 percent power, a 60 percent reduction in incidence of *S. aureus* bacteremia in the vaccine group during an observation window of 3-54 following vaccination. However, since the antibody correlate of protection was not known prior to this study and since antibody levels decline rapidly in ESRD patients, other time windows were evaluated.

Evaluation of efficacy was based on data from two weeks after vaccination. The rate of *S. aureus* bacteremia was compared between the vaccine and control groups by an exact, stratified, person-time incidence calculation using StatXact software. See Software Manual for StatXact-4. Cambridge, Mass.: Cytel, Inc; 1998, and Breslow and Day, Statistical methods in cancer research. Vol. II: The design and analysis of cohort studies. New York: Oxford University Press; 1987. Four cells were created by the two strata defined by baseline nasal carriage and vascular access modality. Time to the first episode of *S. aureus* bacteremia was described by the Kaplan-Meier method and compared by a stratified log-rank test. Repeated measures logistic regression models (SAS PROC GENMOD) were used to describe the time-dependence of the chances of infection, from which time trends in efficacy were estimated. Zeger and Liang, Longitudinal data analysis for discrete and continuous outcomes. *Biometrics* 1986;42:121-30. The model included adjustment for stratum, age, and gender.

An additional analysis, based on a two-sample permutation test, was used to determine the highest vaccine efficacy for any contiguous period during weeks 3-54 of follow-up. Edington E S. Randomization Tests. New York: Marcel Dekker; 1980. A total of 10,000 simulated data sets were generated from all 1798 subjects to examine all possible post-injection periods of at least six months during the 54 weeks after vaccination. P-values for tests of person-time efficacy in contiguous intervals were calculated as the proportion of simulated efficacies greater than the value obtained in the study.

The numbers of subjects who experienced vaccine reactions and deaths in the vaccine and placebo groups were compared by Fisher's exact test. No adjustments were made for the multiplicity of testing of safety.

A total of 1804 of 1991 screened subjects recruited at the 73 hemodialysis centers were randomized and received vaccine (n=894) or placebo (n=910). Among 187 screened subjects who were not immunized, the reasons were failure to meet eligibility criteria or failure to comply with the protocol (n=81), withdrawal of consent (n=71), change in health status (n=22), and other reasons (n=13). The vaccinees and controls contributed a median time on study of 75 weeks and 74 weeks, respectively, with 76 percent of the subjects in each group on study for at least 54 weeks. Six subjects were excluded from the efficacy analyses: Three controls died within the first two weeks, and two vaccinees and one control had infections within two weeks before injection. No subject was excluded from safety evaluations. The two groups were similar in pretreatment demographics and clinical characteristics, and were representative of the diversity of California. The subjects were 33 percent Caucasian, 31 percent Hispanic, 23 percent Black, and 13 percent Asian. Among the 894 vaccinees and 910 controls, there were 46 and 44 percent female subjects, and 52 and 51 percent diabetics, respectively. At vaccination, 69 percent of subjects in both groups had graft access, and 22 percent were nasal carriers in both groups. The mean age in both groups was 58.3 years.

There were no statistically significant differences in the number of deaths between the vaccine and control groups and none were considered related to the vaccine. There was a statistically significant increase in local reactions, malaise, and myalgia, in vaccinees compared with controls (Table 1).

TABLE 3

Summary of Vaccine Reactions*

| Reaction | Vaccine Group (N = 893) | Placebo Group (N = 907) | P Value |
|---|---|---|---|
| Local | | | |
| Induration | 121 (13.5) | 40 (4.4) | <0.001 |
| Erythema | 93 (10.4) | 44 (4.9) | <0.001 |
| Injection site pain | 290 (32.5) | 128 (14.1) | <0.001 |
| Heat | 85 (9.5) | 33 (3.6) | <0.001 |
| Any local reaction | 338 (37.8) | 179 (19.7) | <0.001 |
| Systemic | | | |
| Headache | 243 (27.2) | 227 (25.0) | 0.31 |
| Myalgia | 253 (28.3) | 199 (21.9) | 0.002 |
| Malaise | 226 (25.3) | 188 (20.7) | 0.02 |
| Nausea | 168 (18.8) | 141 (15.5) | 0.07 |
| Vomiting | 64 (7.2) | 73 (8.0) | 0.53 |
| Fever | 41 (4.6) | 42 (4.6) | 1.00 |
| Any systemic reaction | 431 (48.3) | 393 (43.3) | 0.04 |

*Data not recorded for 1 patient in the vaccine group and 3 in the placebo group. Values in parentheses are percent of group. Injection site pain is a composite of ache, burning, and tenderness. P values are from Fisher's exact test comparing the vaccine and placebo groups.

Local reactions were generally mild or moderate and resolved within 2 days. A causative or temporal relationship between *S. aureus* bacteremia and death was identified for 9 of the 152 deaths (5.9 percent) in the vaccine group and 11 of the 146 deaths (7.5 percent) in controls (Fisher's exact test P=0.65).

In weeks 1-2 following vaccination but prior to the onset of vaccine efficacy follow-up, there was one bacteremic patient in the vaccine group and none in the placebo group. In the period from 3 to 40 weeks, there were 11 events in 618.9 person-years in vaccinees and 26 events in 627.0 person-years in controls. The vaccine reduced bacteremias by 57 percent (95 percent confidence interval 10.2 to 80.9, P=0.02). After 40 weeks, efficacy declined, to 26 percent (95 percent confidence interval 24.1 to 56.9, P=0.23; Table 2) at 54 weeks.

TABLE 4

Cumulative Number of Patients Developing S. aureus Bacteremia and Efficacy of Vaccine by Weeks after Injection*

| Weeks after Injection | Vaccine Group | | Placebo Group | | Percent Efficacy (95% CI) | P Value |
|---|---|---|---|---|---|---|
| | No. Inf | Person-Year | No. Inf | Person-Year | | |
| 10 | 4 | 135.2 | 5 | 138.0 | 18% (−279., 83.8) | 1.0 |
| 20 | 6 | 300.6 | 13 | 306.6 | 53% (−32.8, 85.3) | 0.17 |
| 30 | 8 | 461.9 | 22 | 469.7 | 63% (13.8, 85.8) | 0.02 |
| 40 | 11 | 618.9 | 26 | 627.0 | 57% (10.2, 80.9) | 0.02 |
| 50 | 25 | 766.5 | 34 | 775.3 | 26% (−28.4, 57.5) | 0.30 |
| 54 | 27 | 818.4 | 37 | 827.4 | 26% (−24.5, 56.8) | 0.23 |
| 91 | 37 | 1165.0 | 49 | 1161.6 | 25% (−17.8, 52.2) | 0.24 |

*Data are for first episodes of bacteremia among the 1798 patients in the efficacy population. Results from weeks 1 and 2 after injection are excluded. The efficacy of the vaccine is calculated as 100 × (1 − [person-time rate of developing S. aureus bacteremia in vaccine group/person-time rate of developing S. aureus bacteremia in placebo group]). P values are for an exact test of incidence rate ratio = 1 in comparisons between the vaccine and placebo groups.

Using the two-sample permutation test to determine the highest efficacy in a contiguous interval, an efficacy of 75 percent was observed over the period of 187 days (27 weeks) beginning on day 54 after injection, (5 infections in 437.4 person-years in the vaccine group compared with 20 infections in 444.2 person-years in the control group, P=0.01).

Tests for homogeneity of the person-time efficacy during weeks 3 to 91 showed that efficacy was not significantly different across the four cells created by the two strata (P=0.15 for an exact test of homogeneity). However, there was limited power to evaluate this interaction. In both groups, subjects with vascular access via a graft rather than a fistula at the start of the study tended to be at increased risk of bacteremia (Table 3). Nasal carriage of S. aureus also tended to be associated with increased risk of bacteremia in controls (person-time rates 7.6 versus 3.1 per 100 person-years, P=0.06, exact comparison of person-time rates), but not in vaccinees.

TABLE 5

Number and Percentage of Patients Developing S. aureus Bacteremia during Weeks 3–54 by Vascular Access Type, Nasal Carriage Status, and Treatment Group*

| Vascular Access Type and Nasal Carriage Status | Vaccine Group | | Placebo Group | |
|---|---|---|---|---|
| | Total | Infections | Total | Infections |
| Graft, Nasal Carriage Negative | 493 | 18 (3.7) | 496 | 20 (4.0) |
| Graft, Nasal Carriage Positive | 123 | 6 (4.9) | 129 | 10 (7.8) |
| Fistula, Nasal Carriage Negative | 209 | 3 (1.4) | 214 | 2 (0.9) |
| Fistula, Nasal Carriage Positive | 67 | 0 (0) | 67 | 5 (7.5) |

*Values in parentheses are percent of strata.

The vaccine and control groups had a similar distribution of S. aureus types among bacteremic patients. It was not possible to retrieve 13 of 37 isolates in the vaccine group and 12 of 49 in the placebo group for typing. In the vaccine group, 8 (33 percent) were Type 5, and 11 (46 percent) were Type 8. Five (21 percent) were Type 336. In the placebo group, 10 (27 percent) were type 5, 20 (54 percent) were type 8, and 7 (19 percent) were Type 336. Type distribution of S. aureus isolates from bacteremic patients in this study was consistent with results reported by others. Methicillin resistance was found in 7 of 37 S. aureus isolates in the vaccine group and 12 of 48 in the placebo group (one isolate from a control was not tested). The similar distribution of methicillin resistance among isolates from both the vaccine and placebo groups is consistent with in vitro data showing that both antibiotic-resistant and -sensitive S. aureus are killed by antibody-mediated opsonophagocytosis.

Between weeks 3 and 40, there were 37 S. aureus bacteremias (11 in the vaccine group and 26 in the placebo group). It was not possible to retrieve 2 of 11 isolates in the vaccine group and 6 of 26 in the placebo group for typing. In the vaccine group, there were 5 Type 5, 3 Type 8, and 1 Type 336. In the placebo group, there were 6 Type 5, 11 Type 8, and 3 Type 336 (P=0.50, exact chi-square). Between weeks 3 and 54, there were two vaccinees and six placebo patients with more than one bacteremia (P=0.11, exact Cochran-Mantel-Haenszel test).

There were no statistically significant differences in pre-immunization antibody concentrations between the vaccine and placebo groups. Antibody concentrations remained at pre-immunization levels in the placebo group. In the vaccine group, geometric mean antibody concentrations were 230 μg/mL for Type 5 and 206 μg/mL for Type 8 CPS at week 6 (the first time point evaluated), and declined thereafter (Table 4). The percentage of subjects with a peak antibody concentration of at least 80 μg/mL (the estimated protective level) were 80 percent for Type 5 and 75 percent for Type 8. Included among the nonresponders are 27 subjects (3 percent) for whom data were not available.

TABLE 6

Geometric Mean Concentrations of Type 5 CPS and Type 8 CPS Specific Antibodies*

| Evaluation Time | Vaccine Group | | | Placebo Group | | |
|---|---|---|---|---|---|---|
| | N | Type 5 (μg/mL) | Type 8 (μg/mL) | N | Type 5 (μg/mL) | Type 8 (μg/mL) |
| Pretreatment | 892 | 5.9 | 8.6 | 910 | 5.7 | 8.6 |
| Week 6 | 884 | 230 | 206 | 900 | 5.6 | 8.6 |
| Week 26 | 838 | 120 | 100 | 859 | 5.8 | 8.9 |
| Week 54 | 763 | 74.2 | 64.5 | 776 | 5.7 | 8.9 |
| Week 67 | 507 | 78.1 | 65.8 | 512 | 6.2 | 9.4 |

*Pretreatment values missing for 2 patients in the vaccine group. Numbers of patients decrease over time in both groups because of attrition.

The efficacy of the vaccine was no longer statistically significant when the geometric mean antibody concentrations declined below approximately 80 μg/mL. This estimate of a protective level was extracted from interpolation of the data generated prior to, and at 6, 26, and 54 weeks following immunization. For the vaccine and placebo groups, the peak geometric mean antibody concentrations to Type 5 and Type 8 CPS were not significantly different among those individuals with and without bacteremia.

The results demonstrate that a single injection of S. aureus Type 5 and Type 8 conjugate is safe, immunogenic, and protective for approximately 40 weeks against S. aureus bacteremia in an immune-compromised population of patients with ESRD. This population is at especially high risk for *S. aureus* bacteremia. Nearly 90 percent of the hemodialysis patients responded to the vaccine, and over 75 percent achieved antibody concentrations of at least 80 µg/mL (estimated protective level). The decrease in vaccine efficacy after week 40 paralleled the decrease in concentrations of specific antibodies in the subject population. Antibody concentrations decline more rapidly in hemodialysis patients than in healthy subjects. The rapid decline of antibody levels in patients with ESRD can be counteracted by using booster doses of vaccine.

The minimal protective level of antibodies in patients with ESRD was calculated to be approximately 80 µg/mL, which is 2-3 logs higher than the protective levels of CPS antibodies of *Haemophilus influenzae* type b and *Streptococcus pneumoniae*, (0.15 and 1 µg/mL, respectively). The difference in protective antibody level may be attributable to impaired phagocyte function and underlying disease in patients with ESRD. Thus, identification of a protective antibody level for this patient population provides a surrogate for clinical efficacy of this vaccine in other at-risk patients.

Nasal carriage has been associated with an increased risk of *S. aureus* bacteremia among hemodialysis patients. *S. aureus* is the most common pathogen of vascular access site infection, and it is the most frequent cause of access-related bacteremias. Although the numbers are small, it appears that nasal carriage put controls, but not vaccinee, at higher risk of bacteremia. This suggests that vaccination protected against an increased risk of *S. aureus* infection associated with nasal carriage.

Through 40 weeks from vaccination, the bivalent vaccine induced statistically significant protection against all *S. aureus* bacteremias. Efficacy is increased following addition of other antigens, particularly Type 336 antigen.

*S. aureus* Type 5 and Type 8 CPS-recombinant *Pseudomonas aeruginosa* non-toxic exotoxin A (rEPA) conjugate vaccine (StaphVAX®) was evaluated for its safety, immunogenicity, and efficacy in a double-blinded, randomized, placebo-controlled study of end-stage renal disease (ESRD) patients maintained on hemodialysis. Adult patients at 73 hemodialysis centers received a single intramuscular injection of either vaccine (n=894) or saline (n=910). IgG antibodies to Types 5 and 8 CPS were measured at intervals for up to 2 years, and episodes of *S. aureus* bacteremia were recorded. Efficacy was determined by comparing the attack rate of *S. aureus* bacteremia in the vaccine group to that of the controls.

Vaccine reactions were generally mild to moderate and most resolved within 2 days. Each type of CPS elicited a significant antibody response in 86 percent of the patients. At 40 weeks after vaccination, the incidence of *S. aureus* bacteremia was 11/892 in the vaccine group, and 26/906 in controls (person-time estimate of efficacy 57 percent, P=0.02, 95 percent confidence interval, 10 to 81). Vaccine efficacy for longer intervals did not differ significantly from zero. The estimated protective level of CPS-specific IgG was approximately 80 µg/mL. The conjugate vaccine conferred immunity against *S. aureus* bacteremia in hemodialysis patients for approximately 40 weeks after which its efficacy waned paralleling decreasing antibody levels.

The contents of all references mentioned herein are incorporated by reference in their entirety Many modifications and variations may be made to the techniques and structures described and illustrated herein without departing from the spirit and scope of the invention.

What is claimed is:

1. A method of reducing the incidence of *Staphylococcus aureus* infection in an immune-compromised human, comprising administering to an immune-compromised human an immunoprotective amount of a vaccine comprising (i) a glycoconjugate of a Type 5 polysaccharide antigen of *S. aureus* and an immunocarrier and (ii) a glycoconjugate of a Type 8 polysaccharide antigen of *S. aureus* and an immunocarrier.

2. The method according to claim 1, wherein said immune-compromised human is selected from the group consisting of end stage renal disease (ESRD) patients, diabetic patients, the elderly in extended care facilities, patients with invasive surgical procedures, and other patients in acute care settings.

3. The method according to claim 1, wherein said immune-compromised human suffers from end stage renal disease.

4. The method according to claim 1, wherein said immunocarrier is diphtheria toxoid, tetanus toxoid, recombinantly produced, genetically detoxified variants thereof or a recombinantly-produced, non-toxic-mutant of *Pseudomonas aeruginosa* exotoxin A or *Staphylococcus* exotoxin or toxoid.

5. The method according to claim 1, wherein said vaccine additionally comprises an adjuvant or immuostimulant.

6. The method according to claim 1, wherein said vaccine additionally comprises a β-glucan or granulocyte colony stimulating factor.

7. The method according to claim 1, wherein said immunoprotective amount is an amount sufficient to induce in an immune-compromised human a Type 8 IgG antibody concentration of at least 206 µg/mL and a Type 5 IgG antibody concentration of at least 230 µg/mL at 6 weeks post-vaccination.

8. The method according to claim 1, wherein said immunoprotective amount is an amount sufficient to induce in an immune-compromised human a Type 8 IgG antibody concentration of at least 100 µg/mL and a Type 5 IgG antibody concentration of at least 120 µg/mL at 26 weeks post-vaccination.

9. The method according to claim 1, wherein said immunoprotective amount is an amount sufficient to induce in an immune-compromised human a Type 8 IgG antibody concentration of at least 80 µg/mL and a Type 5 IgG antibody concentration of at least 80 µg/mL at 40 weeks post-vaccination.

10. The method according to claim 1, wherein said immunoprotective amount is an amount sufficient to provide protection at 40 weeks post-vaccination.

11. The method according to claim 1, wherein said immunoprotective amount comprises about 100 µg of the Type 5 glycoconjugate and about 100 µg of the Type 8 glycoconjugate.

12. The method according to claim 1, wherein said immunoprotective amount comprises 100 µg of the Type 5 glycoconjugate and 100 µg of the Type 8 glycoconjugate.

13. The method according to claim 1, wherein said immune-compromised human is a diabetic patient.

14. The method according to claim 1, wherein said immune-compromised human is a patient with vascular graft access.

15. The method according to claim 1, wherein said immune-compromised human is an elderly patient in an extended care facility.

16. The method according to claim 1, wherein said immune-compromised human is an invasive surgical procedure patient.

17. The method according to claim 1, wherein said immune-compromised human is a patient in an acute care setting.

18. The method according to claim 1, wherein the vaccine is administered without an adjuvant.

* * * * *